United States Patent
Huang

(12) 
(10) Patent No.: US 7,345,152 B2
(45) Date of Patent: Mar. 18, 2008

(54) MONOCLONAL ANTIBODY SPECIFIC FOR AN EPITOPE OF INACTIVATED FELINE IMMUNODEFICIENCY-ENCODED GLYCOPROTEIN

(75) Inventor: Chengjin M. Huang, Fort Dodge, IA (US)

(73) Assignee: Wyeth, Msdison, NJ (US)

( * ) Notice: Subject to any disclaimer, the term of this patent is extended or adjusted under 35 U.S.C. 154(b) by 0 days.

(21) Appl. No.: 10/648,667

(22) Filed: Aug. 26, 2003

(65) Prior Publication Data

US 2004/0053224 A1    Mar. 18, 2004

Related U.S. Application Data

(60) Provisional application No. 60/410,246, filed on Sep. 12, 2002.

(51) Int. Cl.
*C07K 16/00* (2006.01)
*C12N 5/16* (2006.01)

(52) U.S. Cl. .................... 530/388.3; 435/339

(58) Field of Classification Search ............... 530/808; 435/59, 70.2, 70.21, 351, 7.1, 326, 331, 345; 424/184.1, 130.1, 141.1, 147.1, 148.1
See application file for complete search history.

(56) References Cited

U.S. PATENT DOCUMENTS

| 5,177,014 A * | 1/1993 | O'Connor et al. .......... 435/188 |
| 5,219,725 A | 6/1993 | O'Connor et al. |
| 5,275,813 A * | 1/1994 | Yamamoto et al. ....... 424/208.1 |
| 6,107,077 A | 8/2000 | Yamamoto |
| 6,376,236 B1 | 4/2002 | Dubensky, Jr. et al. |
| 6,383,765 B1 | 5/2002 | Andersen et al. |

FOREIGN PATENT DOCUMENTS

| EP | 997 529 A2 | 5/2000 |
| WO | WO 90/06510 | 6/1990 |
| WO | WO 92/15684 | 9/1992 |
| WO | WO 94/02613 | 2/1994 |
| WO | WO 94/20622 | 9/1994 |

OTHER PUBLICATIONS

Kakinuma et al. Nucleotide sequence of Feline Immunodeficiency virus: Classification of Japanese isolates into two subtypes which are distinct from non-Japanese subtypes. Journal of Virology, Jun. 1995, p. 3639-3646.*

Bendinellli et al., Feline Immunodeficiency Virus: an Interesting Model for AIDS Studies and an Important Cat Pathogen, Clinical Microbiology Review 8:, 1995, pp. 87-112.

Pancino et al, Differences in feline immunodeficiency virus host cell range correlate with envelope fusogenic properties, Virology 206: pp. 796-806, 1995.

Pederson et al., Isolation of a T-lymphotropic lentivirus from domestic cats with immunodeficiency-like syndrome, Science 235: 1987, pp. 790-793.

* cited by examiner

*Primary Examiner*—Bruce Campell
*Assistant Examiner*—Emily M. Le
(74) *Attorney, Agent, or Firm*—Adley F. Mandel; Anne M. Rosenblum

(57) ABSTRACT

The present invention provides a monoclonal antibody specific for an epitope which is unique to the surface protein component of an inactivated feline immunodeficiency virus (FIV) envelope glycoprotein. Said antibody is useful for the quantification of inactivated FIV or the determination of the potency of an inactivated FIV vaccine.

4 Claims, 1 Drawing Sheet

Figure 1:
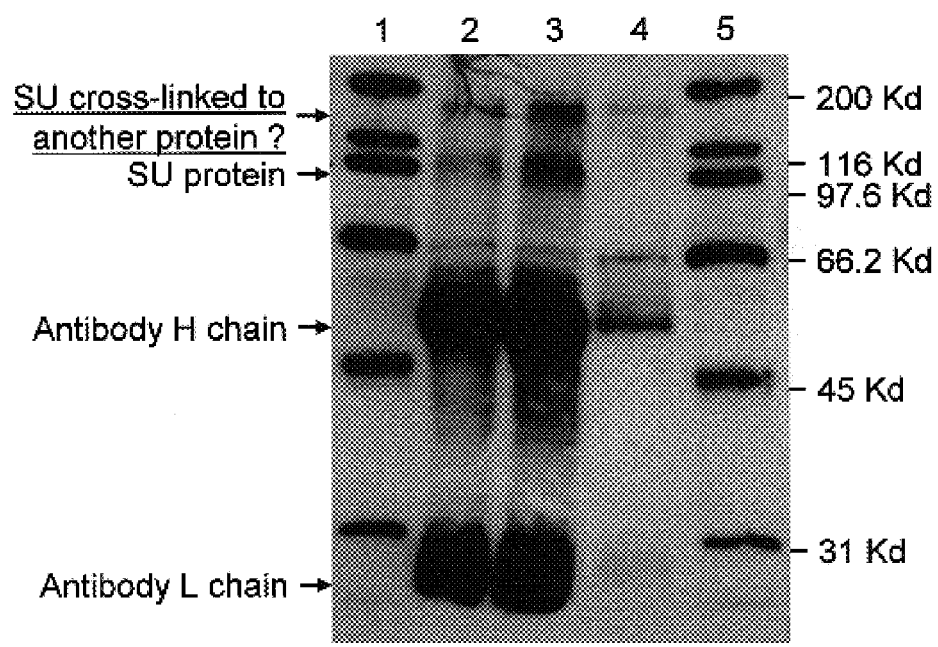

MONOCLONAL ANTIBODY SPECIFIC FOR AN EPITOPE OF INACTIVATED FELINE IMMUNODEFICIENCY-ENCODED GLYCOPROTEIN

BACKGROUND OF THE INVENTION

This application claims priority from copending provisional application Ser. No. 60/410,246, filed on Sep. 12, 2002, the entire disclosure of which is hereby incorporated by reference.

Feline immunodeficiency virus (FIV), originally feline T-lymphotropic lentivirus, was first reported by Pederson et al., Science, (1987) 235:790-793 and has been identified in domestic cats and cheetahs. The infection is endemic in cats throughout the world. Like HIV, FIV is an international concern. According to the American Association of Feline Practitioners, up to one in twelve cats may test positive for FIV. After infection, there is a transient period of fever, lymphadenopathy and neutropenia. Most cats recover from this stage and appear normal for months or years before immunodeficiency occurs. Due to this latent manifestation of immunodeficiency, it would be unduly hazardous to utilize a live virus vaccine for the treatment or prevention of FIV. Although monclonal antibodies specific for epitopes of FIV-encoded antigens or antigenic proteins are known, i.e. U.S. Pat. Nos. 5,177,014 and 5,219,725, these antibodies are not capable of recognizing inactivated FIV. This means that for current, commercial FIV vaccines, all of which utilize inactivated FIV, there are no known monoclonal antibodies useful for the determination of virus quantity or the potency of the inactivated FIV component in a vaccine composition.

Therefore, it is an object of this invention to provide a monoclonal antibody specific for an epitope of an inactivated FIV glycoprotein.

It is another object of this invention to provide a method for the determination of the quantity of an inactivated FIV.

It is a further object of this invention to provide a method to determine the potency of an inactivated FIV vaccine.

It is a feature of this invention that the monoclonal antibody of the invention is specific for the epitope of an inactivated FIV glycoprotein and does not recognize epitopes of live FIV glycoproteins, proteins or antigens.

Further objects and features of the invention will become more apparent from the detailed description set forth herein below.

SUMMARY OF THE INVENTION

The present invention provides a monoclonal antibody specific for an epitope unique to an inactivated feline immunodeficiency virus-encoded glycoprotein.

The present invention further provides a method for the detection of an epitope unique to an inactivated feline immunodeficiency virus-encoded glycoprotein in a sample which comprises: contacting said sample with a monoclonal antibody specific for an epitope unique to an inactivated feline immunodeficiency virus-encoded glycoprotein to form a complex; and detecting said complex.

BRIEF DESCRIPTION OF THE DRAWING

FIG. 1 is a photograph of a Western immunoblot analysis of the monoclonal antibody, mAb 1D9, identified as specific for a unique epitope of an inactivated feline immunodeficiency virus-encoded glycoprotein.

FIG. 1 is further described as follows: Immunoprecipitation of FIV envelope glycoproteins with monoclonal antibody 1D9. A virus stock enriched in formalin-inactivated FIV was biotinylated with sulfo-NHS-LC-biotin, and extracted with Triton X-100. Immunoprecipitation was carried out by incubating the extract with mAb 1D9 or H5332. The immune complexes were collected on Immobilized Protein G, washed and subjected to SDS-PAGE and Western blotting. The proteins on the blot were detected using peroxidase-labeled streptoavidin. Lanes 1 and 5, biotinylated molecular weight marker; lane 2, 20 uL of mAb 1D9 used for immunoprecipitation; lane 3, 100 uL of 1D9 used for immunoprecipitation; lane 4, 100 uL of an irrelevant monoclonal antibody, H5332, used in immunoprecipitation. The H (50Kd) and L chains (25 Kd) of the antibodies and some BSA (67 Kd) were non-specifically stained by peroxidase-labeled streptoavidin.

DETAILED DESCRIPTION OF THE INVENTION

The feline immunodeficiency virus (FIV) envelope glycoprotein is involved in receptor interactions with cells and this interaction determines the cells susceptability to said virus. The FIV envelope glycoprotein is also involved in virus penetration and syncytium formation and is the primary target for humoral and cellular immune responses. (Bendinelli, M., et al., Clinical Microbiology Review, (1995) 8:87-112) Said envelope glycoprotein consists of two components which are non-covalently bound in the virion, the surface (SU) protein which is heavily glycosylated and has an apparent molecular weight of 95,000-100,000 and the trans-membrane (TM) protein which is less glycosylated and has an apparent molecular weight of 35,000-40,000. (Pancino, G. et al., Virology, (1995) 206:796-806). Various studies have suggested that the FIV envelope protein is capable of inducing protective FIV immunity in cats. Therefore, an enzyme-linked immunosorbent assay (ELISA) which measures the relative quantity or purity of the FIV envelope protein would be most useful for determining the potency of an FIV vaccine. However, all current commercially available FIV vaccines utilize inactivated or killed virus and the monoclonal antibodies known to react with or recognize FIV or FIV glycoprotein do not react with or recognize inactivated FIV or FIV glycoprotein. It is proposed that the inactivation of said virus may alter the conformation of the FIV envelope protein.

Surprisingly, it has now been found that the monoclonal antibody, designated mAb 1D9, specifically recognizes only inactivated FIV and does not recognize live FIV. Further, ELISA and immunoprecipitation experiments demonstrate that the monoclonal antibody of the invention reacts specifically with the surface protein component of the FIV envelope glycoprotein.

The term monoclonal antibody, as used in the specification and claims, designates an antibody produced from a single antibody-producing cell which has been cloned to produce an antibody-producing cell line. The term epitope designates a specific amino acid sequence, modified amino acid sequence, or protein secondary or tertiary structure which is recognized by an antibody. The term inactivated virus designates “not live” or “killed” virus.

The monoclonal antibody of the invention may be prepared using conventional techniques known in the art. For example, mice may be immunized with a partially purified, inactivated virus such as FIV-Shiz, FIV-Petaluma, or the like, preferably FIV-Shiz; mouse tail bleeds are then screened for antibody response and selected for fusion; cloned hybridoma cells are then selected and screened for specific reactivity with inactivated FIV. The hybridoma for the single stable clone thus obtained may be grown in a bioreactor and multiple harvests of the antibody may be pooled to generate the desired monoclonal antibody, mAb 1D9.

Said antibody may be produced by a cell line deposited on Dec. 3, 2002 in the American Type Culture Collection (ATCC), 10801 University Boulevard, Manassas, Va. 20110-2209, U.S.A. and given ATCC Accession No. PTA-4837. The deposit was made under the conditions mandated by 37 C.F.R. § 1.808 and is being maintained pursuant to the Budapest Treaty.

Inactivation of the virus may be achieved by conventional inactivating means, for example chemical inactivation using chemical inactivating agents such as binary ethyleneimine, phenol, α-lactopropianate, beta-propiolactone, formalin, merthiolate, gluteraldehyde, sodium dodecyl sulfate, or the like or a mixture thereof, preferably formalin. Said virus may also be inactivated by heat or psoralen in the presence of ultraviolet light.

The monoclonal antibody of the invention is specific for inactivated FIV and forms a sufficiently strong interaction with an epitope unique to an inactivated FIV envelope glycoprotein, such as gp 95 or gp 130, to be useful in an assay for the determination of the quantity of an inactivated virus or for the potency of an inactivated FIV vaccine. Accordingly, the present invention provides a method for the detection of an epitope unique to an inactivated FIV-encoded glycoprotein in a sample which comprises: contacting said sample with a monoclonal antibody specific for an epitope unique to an inactivated FIV-encoded glycoprotein to form a complex; and detecting said complex.

Samples suitable for use in the method of the invention include those which contain an inactivated virus or inactivated virus-infected cells in a culture medium or in a vaccine composition.

Means of detecting the complex suitable for use in the method of the invention include any conventional means generally used to detect monoclonal antibody protein complexes such as detection by enzyme-, fluorochrome-, or biotin-labeled anti-mouse antibody, detection by Protein A, or the like. In actual practice, the method of the invention may be implemented in the form of an ELISA or immunoprecipitation assay having the monoclonal antibody, mAb 1D9, as the detection antibody.

For a more clear understanding of the invention, the following examples are set forth below. These examples are merely illustrative and are not understood to limit the scope or underlying principles of the invention in any way. Indeed, various modifications of the invention, in addition to those shown and described herein, will become apparent to those skilled in the art from the examples set forth hereinbelow and the foregoing description. Such modifications are also intended to fall within the scope of the appended claims.

Unless otherwise noted, all parts are parts by weight.

EXAMPLE 1

Preparation of a Monoclonal Antibody Specific for an Epitope of an Inactivated FIV-Encoded Glycoprotein Cells and Viruses FIV-Shizuoka (FIV-Shiz, a subtype D FIV) was propagated in persistently infected lymphoid cell lines, derived from FIV-Shizuoka and FeT-J (ATCC Accession No. CRL 11967), an IL-2 independent cell line, designated Shiz. An FIV-Shizuoka persistently infected cell line is also deposited at ATCC under Accession No. CRL 11976. To generate antigen stocks, virus fluids were inactivated using formalin and concentrated using ultrafiltration.

Antigen stocks are also similarly prepared from a variety of other FIV strains and subtypes, such as, field isolates, FIV strain NCSU 1 (ATCC Accession No. VR-2333), FIV strain UC24818 (ATCC Accession No. VR-2619), FIV-Petaluma (subtype A, ATCC Accession No. VR-2186), FIV-Dixon (subtype A), FIV-UK8 (subtype A), FIV-Bangston (subtype B), FIV-Amori-1 (subtype B), FIV-Amori-2 (subtype B), propagated on appropriately susceptible cell lines and IL-2 dependent or independent feline T-cell lines, such as, PMBCs, CRFK, NYA-1 (ATCC Accession No. CRL-2417), FeT-1M (ATCC Accession No. CRL-10775), FeT-2D (ATCC Accession No. 10774), Fet-1C (ATCC Accession No. CRL-11968), FL-4 (ATCC Accession No. 10772), FL-6 (ATCC Accession No. 10773), or propagated on FIV persistently infected cell lines derived therefrom, such as, the FIV-CRFK cell line having ATCC Accession No. VR-1312, the FIV-Bangston infected cell line deposited under ATCC Accession No. 11975, and the like, such as those disclosed, for example, in U.S. Pat. No. 6,254,872.

Generation of Monoclonal Antibody

Balb/c mice were immunized twice with formalin-treated FIV-Shiz virus which is purified using glycerol gradient technique. The injection site was subcutaneous for both injections. Mouse tail bleeds are screened for antibody response. One mouse which displayed high FIV-specific antibody titers was chosen for fusion. Splenocytes collected from this mouse were fused to SP2/0 myeloma cells. Hybridoma cells were selected as described in "Antibodies: A Laboratory Manual" by Ed Harlow and David Lane for Cold Spring Harbor Press. Primary hybridoma clones were screened for specific reactivity with formalin-treated FIV-Shiz. One stable clone, mAb 1D9, was obtained. The hybridoma for mAb 1D9 was grown in a Heraeus miniPERM bioreactor. Multiple harvests of the antibody were obtained and pooled to generate a large quantity of mAb 1D9.

EXAMPLE 2

Use of Monoclonal Antibody, mAb 1D9, as a Detection Antibody in an Enzyme-Linked Immunosorbent Assay In this evaluation, Galanthus Nivalis Agglutinin (GNA) is used to capture the glycoproteins. This GNA ELISA combines the high selectivity of GNA binding with its broad reactivity with the glycoproteins of HIV-1, HIV-2, SIV and FIV. To begin, ninety-six microwell plates were coated with 10 μg/mL of GNA in 50 mM carbonate, pH 9.6 for 1 h at 37° C. After blocking wells with PBS-10% FBS for 2 h at 37° C., samples which were treated with 1% Empigen BB (Calbiochem) for 1 h at 37° C. were added, and incubated for 2 hours at 37° C. Unbound antigens were removed by washing 3 times with PBS containing 0.1% Tween 20. The monoclonal antibody of Example 1, mAb 1D9 diluted at 1:8,000 was added to each well and the plate was incubated at 37° C. for 1 h. After washing, peroxidase-labeled goat anti-mouse IgG, Kirkegaard & Perry Laboratories (KPL), diluted 1:1,000 was added and the plate was incubated at 37° C. for 1 h, and then washed and developed with TMB peroxidase substrate (KPL). The plate was read at 650 nm minus 490 nm after a 5 min reaction period.

EXAMPLE 3

Use of Monoclonal Antibody, mAb 1D9, as a Detection Antibody in an Immunoprecipitation Assay In this evaluation, a virus stock enriched for the formalin inactivated FIV-Petaluma virus (0.38 mg total protein with less than 5% being FIV proteins) was incubated with 5 mg of sulfo-NHS-LC-biotin (Pierce) in 2 mL of PBS on ice for 1 h. After removing the unincorporated biotin reagent by dialysis, the virus-containing sample was extracted for 1 h with 1% Triton X-100 in 12 mL of PBS, and centrifuged at 100,000 g for 2 h. The supernatant was recovered and used for immunoprecipitation. Immunoprecipitation was carried out by incubating 600 μL of the extract with 80 μL of either mAb 1D9 or mAb H5332 at 4° C. for 1 h. The mAb H5332, which has a specificity for Borrelia OspA protein, was used as the irrelevant antibody control. The immune complexes were collected on Immobilized Protein G (Pierce), washed 4 times with cold PBS-1% NP-40, resuspended in Laemmli buffer and subjected to SDS-PAGE and Western blotting. The blot was blocked for 60 min with SuperBlock (Pierce) and then incubated for 45 min with peroxidase-labeled streptoavidin (KPL), diluted 1:400,000. The membrane was washed 4 times with PBS-0.05% Tween-20, and the biotin-streptoavidin complexes were detected with the SuperSignal chemilluminescence detection kit (Pierce) followed by exposure to X-ray film.

EXAMPLE 4

Evaluation of the Specificity of the Monoclonal Antibody, mAb 1D9

Cells and Viruses

FIV-Shizuoka (FIV-Shiz) and FIV-Petaluma were propagated in persistently infected lymphoid cell lines designated Shiz and FL-6, respectively. Feline leukemia virus (FeLV) was propagated in a chronically infected cell line. Feline calicivirus (FCV), feline viral rhinotracheitis virus (FVR) and feline panleukopenia virus (FPV) were grown on Crandell feline kidney cells. To generate antigen stocks, virus fluids were inactivated with formalin and concentrated using ultrafiltration.

Evaluation

In this evaluation, the specificity of mAb 1D9 was determined using both of the ELISA and immunoprecipitation techniques described hereinabove in Examples 2 and 3.

A—GNA ELISA

Various antigen samples were tested using the assay described in Example 2. The results are shown in Table I below.

TABLE I

| Antigen Sample | Antigen Sample Concentration | Optical Density $A_{650}$-$A_{492}$ Value |
|---|---|---|
| FIV-Shiz virus, inactivated | 1x | 0.572 |
| FIV-Petaluma virus inactivated | 1x | 0.385 |
| FIV-Shiz virus, live | 1x | 0.006 |
| FIV-Petaluma virus, live | 1x | 0.006 |
| FetJ TCS, inactivated | 1x | 0.027 |

TABLE I-continued

| Antigen Sample | Antigen Sample Concentration | Optical Density $A_{650}$-$A_{492}$ Value |
|---|---|---|
| FeLV, inactivated | 1x | 0.020 |
| FCV, inactivated | 1x | 0.027 |
| FVR, inactivated | 1x | 0.027 |
| FPV, inactivated | 1x | 0.026 |
| FeLV, live | $10^{6.63}$ TCID$_{50}$/mL | 0.039 |
| FCV, live | $10^{7.67}$ TCID$_{50}$/mL | 0.035 |
| FVR, live | $10^{7.46}$ TCID$_{50}$/mL | 0.039 |
| FPV, live | $10^{6.75}$ TCID$_{50}$/mL | 0.051 |
| No antigen control | 0 | 0.033 |

Observations

When used at 1:8000 dilution, mAb 1D9 reacted well with both inactivated FIV-Shiz and inactivated FIV-Petaluma samples. In contrast, mAb 1D9 showed no reaction when it was tested with samples of either live FeLV, FCV, FVR and FPV or inactivated antigen stocks for those various viruses. Advantageously, mAb 1D9 does not react with samples of live FIV-Petaluma or live FIV-Shizuoka even though it reacts well with samples of both inactivated FIV-Shiz and inactivated FIV-Shiz. The ELISA data in Table I indicated that the GNA ELISA based on the monoclonal antibody mAb 1D9 may be used to detect specifically the FIV glycoprotein. The observation that mAb 1D9 reacted with formalin-inactivated FIV, not live FIV, indicates that the epitope recognized by mAb 1D9 is a unique epitope created by the formalin treatment of FIV.

B—Immunoprecipitation

To further confirm the specificity of mAb 1D9 for the inactivated FIV envelope glycoprotein, an inactivated FIV-enriched stock was biotinylated and immunoprecipitated as described in Example 3 with mAb 1D9 or mAb H5332, an irrelevant monoclonal antibody. As shown in FIG. 1, mAb 1D9 reacted specifically with the SU protein, as indicated by the broad 95-100 Kd band. The band with a higher molecular weight (ca. 160 Kd) might be a complex of SU with another protein which was cross-linked by formalin treatment.

CONCLUSION

The results of ELISA and immunoprecipitation experiments demonstrated that the monoclonal antibody mAb 1D9 reacted specifically with the surface protein component of the FIV envelope glycoprotein, and is suitable for use in a potency test for inactivated FIV vaccines or for the determination of the quantity of an inactivated virus sample or an inactivated virus-infected cell sample.

What is claimed is:

1. Monoclonal antibody produced from the cell line deposited at the American Type Culture Collection (ATCC) under Accession No. PTA-4837.

2. A method for the detection of an epitope of an inactivated FIV-encoded glycoprotein in a sample comprising: contacting said sample with a monoclonal antibody produced from the cell line deposited at the American Type Culture Collection (ATCC) under Accession No. PTA-4837 or a clone thereof, wherein the monoclonal antibody specifically reacts with or recognizes the epitope of the inactivated FIV or inactivated FIV glycoprotein but does not react with or recognize live FIV or live FIV glycoprotein, to form a complex; and detecting said complex.

3. A hybridoma cell line deposited at the American Type Culture Collection under Accession No. PTA-4837, suitable for obtaining monoclonal antibodies specific for an epitope of an inactivated FIV-encoded glycoprotein, prepared by immunizing a suitable host with a partially purified, inactivated FIV, screening the host for high FIV-specific antibody response, fusing splenocytes from said host with a suitable myeloma cell line, and screening hybridomas for specific reactivity with inactivated FIV wherein there is no reaction with or recognition of live FIV.

4. The cell line deposited at the American Type Culture Collection under Accession No. PTA-4837.

* * * * *